United States Patent [19]

Machiele

[11] 3,962,273

[45] June 8, 1976

[54] NOVEL METHOD FOR THE SYNTHESIS OF 4-THIO AND 4-SELENO ETHERS OF 2-PYRAZOLIN-5-ONES

[75] Inventor: Delwyn E. Machiele, Rochester, N.Y.

[73] Assignee: Eastman Kodak Company, Rochester, N.Y.

[22] Filed: Sept. 1, 1972

[21] Appl. No.: 285,687

[52] U.S. Cl............... 260/308 D; 260/309.2; 260/307 D; 260/306.6 R; 260/307 G; 260/308 R; 260/302 H; 260/307 R; 260/294.8 G; 260/295 AM; 260/244 R; 260/310 A

[51] Int. Cl.$^2$............... C09D 231/08; C07D 257/06

[58] Field of Search........ 260/308 D, 310 A, 607 R, 260/608

[56] References Cited
UNITED STATES PATENTS 3,479,369   11/1969   Ariyan.......................... 260/310 A

*Primary Examiner*—Henry R. Jiles
*Assistant Examiner*—Robert T. Bond
*Attorney, Agent, or Firm*—J. G. Levitt

[57] ABSTRACT

Method for synthesizing 4-substituted thiol and 4-substituted seleno-2-pyrazolin-5-ones by reaction of an appropriate thiol or selenol compound with a 4,4-dihalo-2-pyrazolin-5-one.

16 Claims, No Drawings

NOVEL METHOD FOR THE SYNTHESIS OF 4-THIO AND 4-SELENO ETHERS OF 2-PYRAZOLIN-5-ONES

The invention relates to a process for synthesizing thio and seleno ether derivatives of 5-pyrazolones. In particular, this invention relates to an efficient one step process for obtaining 4-substituted thio- and seleno ether derivatives of 2-pyrazolin-5-one compounds.

Some thio ether products of the above-described type are known in the color photographic art as DIR (Development-Inhibitor Releasing) or as BIR (Bleach Inhibitor Releasing) couplers. Such compounds have been previously prepared, for instance, by reacting a halo substituted coupler with a cuprous aryl mercaptide or by condensation of a heterocyclyl sulfenyl halide with a 4-unsubstituted coupler moiety. The later process is used, for instance, in Column 38 (Coupler LXV) of U.S. Pat. 3,227,551. Known art processes, however, cannot always be successfully or efficiently used, due to a tendency to synthesize relatively large amounts of dimers and other undesired by-products. Although substituted heterocyclyl sulfenyl halides can normally be prepared and readily condensed with 2-pyrazolin-5-ones, it is difficult and sometimes impossible to obtain a heterocyclyl sulfenyl halide having one or more active hydrogen atoms. In this respect, the instant process is believed to represent the only practical method for obtaining certain corresponding 4-substituted ethers. In any case, an efficient one-step process is particularly useful in obtaining a DIR-type coupler such as a 4-benzothiazolythio (or seleno)-substituted 5-pyrazolone.

It is an object of the present invention to efficiently and economically produce 2-pyrazolin-5-one-thio or seleno-ether derivatives.

In addition, it is an object to obtain a class of 4-heterocyclyl substituted magenta dye-forming couplers which cannot be readily obtained by simple condensation reaction with a sulfenyl halide in the usual way.

These and other objects of the present invention are obtained by reacting together, preferably in an organic solvent system, a 4,4-dihalo-2-pyrazolin-5-one such as a 4,4-dibromo-2-pyrazolin-5-one with a thiol or selenol having the structure required to yield the desired 4-substituted 2-pyrazolone-5-one; in particular, the thiol or selenol material should have the formula $$R^3\text{---}R^4H$$

wherein $R^4$ is defined as —S— or —Se—; and
$R^3$ is defined as a heterocyclic group, an aryl group or an alkyl group.

This reaction is further conveniently described as follows:

I.

wherein
COUP is defined as a ballasted or unballasted magenta dye-forming 5-pyrazolone coupler group having the two bromine atoms and the —$R^4$—$R^3$ group, where appropriate, attached at the No. 4 position on the pyrazolone ring; such groups being exemplified or otherwise suggested, for instance, in U.S. Pat. Nos. 2,725,292, 2,772,161, 2,895,826, 2,908,575, 2,920,961, 2,933,391, 2,983,608, 3,005,712, 3,006,759, 3,062,653, 3,148,062, 3,152,896, 3,214,437, 3,227,554, 3,253,924, 3,311,476, 3,419,391, 3,432,521, and 3,519,429;

$R^4$ is defined as above; and
$R^3$ is also generically defined as above, including 1. a heterocyclic group having 5–6 atoms in a heteronucleus containing at least one sulfur, nitrogen or oxygen atom; such group includes, for instance, a benzoxazole group, a benzothiazole group, a benzimidazole group, an oxadiazole group, a thiadiazole group, a triazole group, a phenyl-substituted tetrazole group, a furanyl group, a benzofuranyl group, an oxazolyl group, a pyranyl group, an oxazinyl group, or a pyridyl group, including substituted heterocyclics such as alkyl, halo, hydroxyl, carboxyl, sulfo, amido, etc.;

2. an aryl group such as a phenyl group or a naphthyl group which is optionally substituted by one or more nitro groups such as 2-nitrophenyl, substituted by alkyl carbamyl group of 1–20 carbons such as an eicosylcarbamyl phenyl group by an amino group including alkyl amino phenyl, an alkoxy group of 1–20 carbons such as eicosyloxy, octadecyloxyphenyl, or methoxyphenyl; and 3. an alkyl group such as alkyl of 1–20 carbon (Ex. methyl, isopropyl, eicosyl);

groups (1)–(3) being exemplified, for instance, in U.S. Pat. Nos. 3,227,554, 3,227,551, 3,148,062 3,615,056.

This process of the present invention is further conveniently expressed in accordance with the following equation:

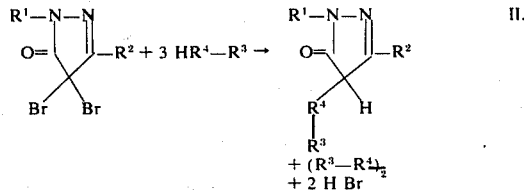

wherein $R^1$ and $R^2$ can be the usual coupler ballasting or other groups such that
$R^1$ is defined
i. as hydrogen,
ii. as an aryl group inclusive of a phenyl or a naphthyl radical exemplified by the following formula when $R^1$ is phenyl

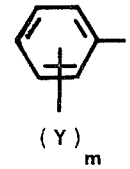

in which Y is individually defined as a halo group such as chloro or bromo, an alkyl group of 1–18 carbons such as methyl or octadecyl, as an alkoxy group of 1–15 carbons, as a cyano group, as a nitro group or combination thereof; and $m$ is defined as 0–5, $m$ values of 2–3 being particularly preferred;
iii. as an alkyl group including an alkyl group of 1–20 carbon atoms such as methyl, isopropyl, and eicosyl;
iv. as an aryl carbonamido group inclusive of a phenyl carbonamido group and optionally substituted by additional groups on the aryl ring, the additional groups being exemplified by an alkylcarbonamido such as a phenoxyalkylcarbonamido including a di-(t)-amyl-phenoxyalkyl carbonamido-substituted-phenyl-carbonamido group;

v. as an amino group including substituted amines such as aryl amines (ex. phenylamino or a naphthyl amino group), the aryl ring of the arylamine being optionally further substituted by an alkylcarbonamido group inclusive of a phenoxy lower alkylcarbonamido group; and vi. as a heterocyclic group having from 5–6 atoms in a heteronucleus and containing at least one oxygen, sulfur or nitrogen atom exemplified by a 2-thiazolyl group, a 2-benzothiazolyl group a 2-benzoxazolyl group, a 2-oxazolyl group, and a 2-benzimidozole group; and $R^2$ is defined i. as an alkyl group, including an alkyl group of 1–20 carbon atoms such as methyl, isopropyl and eicosyl;

ii. as an arylamino group such as a phenylamino group, including substituted arylamino group such as a halophenylamino, a nitrophenylamino, a cyanophenylamino; and a iii. as an alkylcarbonamido group, including substituted alkylcarbonamido such as alkylphenoxy lower alkylcarbonamido exemplified by p-octadecylphenoxybutylcarbonamido;

iv. as an arylcarbonamido group such as a phenylcarbonamido group which can be optionally substituted on the aryl ring with an alkylcarbonamido, particularly a phenoxyalkylcarbon-amido group; and v. as a heterocyclic group having a 5–6 membered heteronucleus such as defined for $R^1$ and $R^3$; and $R^3$ and $R^4$ are the same as defined in formula I, above. Additional suitable ballasting groups are disclosed, for instance, in U.S. Pat. No. 3,615,506.

The described synthesis is preferably effected under "mild reaction conditions" which are defined as preferably utilizing atmospheric pressure with a reaction temperature generally varying from about 10°C.–70°C., preferably from 15°C.–50°C. and in the presence of an inert organic reaction solvent. Such solvents in which both reactants can be dissolved at about 10°–70°C preferably to the extent of at least 1 weight percent, include, for instance, acetonitrile and tetrahydrofuran.

It is also found for purposes of this invention that the term "reactive proportions" covers molar ratios of 4,4 dibromo reactant-to-thiol or selenol reactant of from about 1:1 to about 1:5, a ratio of 1:3 being preferred.

The present processes can be carried out where at least one of the reactants is present in the reaction medium in an amount equal to at least 0.001 moles, said reaction medium being an inert organic solvent in which the reactants are dissolved. Timewise, the above-reaction may vary from about one-half hr. to about 20 hours depending on the temperature and/or pressure conditions utilized.

For purposes of further description of the reaction, both in terms of reactants used and compounds obtained, reference is made to Equation II and Table A below.

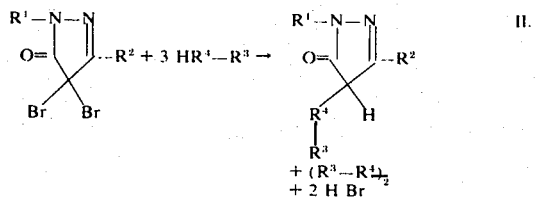

TABLE A

| Coupler No. | $R^1$ | $R^2$ | $R^3$ | $R^4$ |
|---|---|---|---|---|
| 1 | Cl-⟨Cl,Cl⟩ (2,4,6-trichlorophenyl) | -NH-⟨Cl,Cl⟩ (2,4-dichlorophenyl) | -C(=N-N)(N-N-phenyl) (1-phenyl-tetrazolyl) | -S- |
| 2 | '' | -NH-⟨ ⟩-SO₂CH₃ | '' | '' |
| 3 | '' | -NH-⟨CN⟩-CN | '' | '' |
| 4 | '' | -NH-⟨ ⟩-Cl | '' | '' |
| 5 | '' | -NH-⟨Cl,NO₂⟩ | '' | '' |
| 6 | '' | -NH-⟨ ⟩-Cl | '' | -Se- |

TABLE A—Continued

| Coupler No. | R¹ | R² | R³ | R⁴ |
|---|---|---|---|---|
| 7 | " | -NH-CO-C₆H₃(NH-CO-CH₂-O-C₆H₃((t)C₅H₁₁)(C₅H₁₁(t))) | " | -S- |
| 8 | C₆H₅- | -NH-CO-C₆H₃(NH-CO-CH₂-O-C₆H₃((t)C₅H₁₁)(C₅H₁₁(t))) | 1-phenyl-tetrazol-5-yl | -S- |
| 9 | " | " | " | -Se- |
| 10 | 2,5-dichlorophenyl | " | benzimidazol-2-yl | -S- |
| 11 | " | " | " | -Se- |
| 12 | " | " | 5-(C₁₅H₃₁-CO-NH)-benzoxazol-2-yl | -S- |
| 13 | (t)C₄H₉-C₆H₄-O- | -NH-CO-CH(CH₃)-O-C₆H₄-(CH₃CH₂CH₂CH₂-) | C₆H₅- | -S- |
| 14 | NaO₃S-C₆H₄- | -NH-C₆H₄-SO₃Na | C₆H₄(CONH-C₁₈H₃₇)- | " |
| 15 | " | " | " | -Se- |
| 16 | 2,4,6-trichlorophenyl | -NH-C₆H₄-CN | benzothiazol-2-yl | -S- |

TABLE A —Continued
| Coupler No. | R¹ | R² | R³ | R⁴ |
|---|---|---|---|---|
| 17 | " | " | " | " |
| 18 |  | –NH–CO–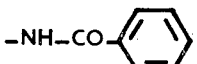–C₁₈H₃₇ | –O–C₁₈H₃₇ | " |
| 19 | " | " | " | –Se– |
| 20 | 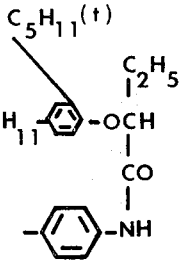 (t)C₅H₁₁ / C₅H₁₁(t) –OCH(C₂H₅)–CO–NH– |  –N⟨S⟩ | 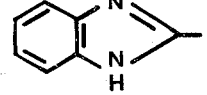 benzimidazole-CH₃ | –S– |
| 21 | " | " | 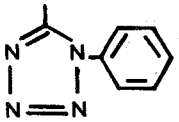 tetrazole-CH₃, N-phenyl | –Se– |
| 22 | C₂₀H₄₁– | –N⟨S⟩  | " | –S– |
| 23 | CH₃–CH(CH₂CH₃)–(CH₂)₆–CH₂– | –NH₂ | " | " |
| 24 | CH₃–(CH₂)₃–O–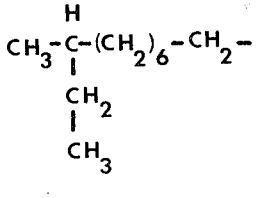– | –NH–CO–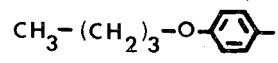–C₁₈H₃₇ | 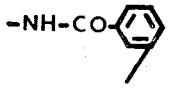 | –Se– |
| 25 | 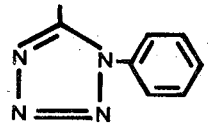 NH–⟨⟩–N(H)–, CO–C₁₈H₃₇ | –NH–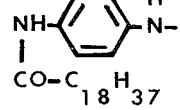(Cl,Cl) | " | –S– |
| 26 | 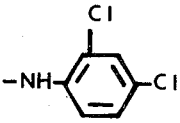 HN⟨piperazine⟩N– | " | " | –Se– |

The invention is further described, although not limited by the following examples.

EXAMPLE I

To 1.2 Grams (2.05 × 10⁻³mol) of 1-(2,4,6-trichlorophenyl)-3-(2,4-dichloroanilino)4,4-dibromo-5-pyrazolone* dissolved in 80 ml acetonitrile were added 1.1 gm (6.2 × 10⁻³mol) of 1-phenyl-5-tetrazolylthiol dissolved in 20 ml of acetonitrile. The yellow color of the 4,4-dibromo reactant is immediately discharged and the mixture allowed to stand for 16 hours at 20°C., then concentrated and the resulting precipitated product recrystallized from acetonitrile and identified as Coupler No. 1 (Table A supra; M.P. 172°C.).

*(obtained by conventional dibromination of coupler 6 in U.S. Pat. 3,152,896)

EXAMPLE II

To 7 Grams (.01 mol) of 1-[α-(2,4-di-(t)-amylphenoxy)butyramido phenyl]-3-N-pyrrolyl-4,4-dibromo-5-pyrazolone(**) dissolved in 200 ml tetrahydrofuran were added with stirring 4.5 grams (0.03 mole) of 2-benzimidazole thiol dissolved in 100 ml tetrahydrofuran; this reaction mixture was then stirred for 2½ hours at 50°C. The solids were filtered off and the filtrate dried. The 4-substituted product was then recrystallized from acetone and identified as Coupler No. 20 (Table A supra; M.P. 185°–186°C.).

**(obtained by conventional dibromination of coupler 22 in U.S. Pat. 3,615,506)

EXAMPLE III

To 16 Grams (.02 mole) of 1-[4-α-(2,4-di-(t)-amylphenoxy)butyramidophenyl]-3-pyrrolyl-4,4-dibromo-5-pyrazolone (partly dissolved in tetrahydrofuran) were solwly added 14 grams (0.06 mole) of 1-phenyl-tetrazolyl-5-selenol dissolved in tetrahydrofuran with agitation at 20°C. The reaction product was filtered to remove insoluble non-coupling material and the filtrate was then added to ligroin. The resulting yellow solid was isolated and identified as Coupler No. 21 (Table A supra; M.P. 134°–146°C.).

The invention has been described in detail with particular reference to certain preferred embodiments thereof, but it will be understood that variations and modifications can be effected within the spirit and scope of the invention.

I claim:

1. A process for obtaining a 4-thio- or a 4-seleno ether derivative of a 2-pyrazolin-5-one compound comprising reacting in reactive proportions in an inert organic reaction solvent and under mild reaction conditions a 4,4-dibromo-2-pyrazolin-5-one with a compound of the formula $R^3—R^4H$ wherein $R^4$ is defined as —S— or —Se—; and $R^3$ is defined as a heterocyclic group having 5–6 atoms in a heteronucleus containing at least one sulfur, nitrogen, or oxygen atom; an aryl group; or an alkyl group, whereby said 4-thio- or 4-seleno-ether derivative of said 2-pyrazolin-5-one compound is produced.

2. A process of claim 1 wherein $R^4$ is —S—.
3. A process of claim 1 wherein $R^4$ is —Se—.
4. A process for obtaining an ether compound of the formula

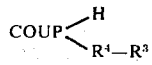

comprising contacting at a temperature of from about 10°C to about 70°C a reactive amount of a dibromo compound of the formula COUP—(Br)₂ wherein
COUP is defined as a ballasted or unballasted magenta dye-forming 5-pyrazolone coupler group having the two bromine atoms and the —$R^4$—$R^3$ group attached to the No. 4 ring position; with a thiol or seleno compound of the formula $R^3—R^4H$ wherein
$R^4$ is defined as —S— or —Se—; and
$R^3$ is defined as a heterocyclic group having 5–6 atoms in a heteronucleus containing at least one sulfur, nitrogen, or oxygen atom, or an aryl group; the reaction of said dibromo compound with said thiol or selenol compound being effected in an inert organic solvent; and thereafter recovering said ether compound from the resulting reaction mixture.

5. A process of claim 4 wherein
$R^4$ is —S—; and
$R^3$ is a benzoxazole group, a benzothiazole group, a benzimidazolyl group, an oxadiazole group, a thiadiazole group, a triazole group, a phenyl-substituted tetrazole group, a furanyl group, a benzofuranyl group, an oxazolyl group, a pyranyl group, an oxazinyl group or a pyridyl group.

6. A process of claim 4 wherein
$R^4$ is —Se—; and
$R^3$ is a benzoxazole group, a benzothiazole group, a benzimidazolyl group, an oxadiazole group, a thiadiazole group, a triazole group, a phenyl-substituted tetrazole group, a furanyl group, a benzofuranyl group, an oxazolyl group, a pyranyl group, an oxazinyl group or a pyridyl group.

7. A process of claim 5 wherein the reaction is effected in tetrahydrofuran at a temperature of about 15°C.–50°C.

8. A process of claim 5 wherein the reaction is effected in acetonitrile at a temperature of about 15°C.–50°C.

9. A process of claim 6 wherein the reaction is effected in tetrahydrofuran at a temperature of about 15°C.–50°C.

10. A process of claim 6 wherein the reaction is effected in acetonitrile at a temperature of about 15°C.–50°C.

11. A process for obtaining 1-(2,4,6-trichlorophenyl)-3-(2,4-dichloroanilino)-4-(1-phenyl tetrazolylthio)-5-pyrazolone comprising contacting (a) 1-(2,4,6-trichlorophenyl)-3-(2,4-dichlorophenylanilino)-4,4-dibromo-5-pyrazolone with (b) a compound of the formula

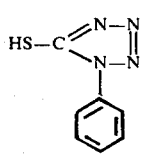

in a weight ration of (a) to (b) respectively of from about 1:1 to about 1:5 in an acetonitrile reaction solvent, and recovering the resulting thioether product.

12. A process as in claim 11 wherein the molar ratio of (a) to (b) is about 1:3.

13. A process for obtaining 1-[4-α-(2,4-di-(t)-amylphenoxy butyramidophenyl]-3-pyrrolyl-4-(2-benzimidazolyl thio)-5-pyrazolone comprising contacting about .01 mole of the 4,4-dibromo precursor with about 0.03 mole of 2-benzimidazole thiol dissolved in tetrahydrofuran as reaction solvent in a molar ratio of (a) to (b), respectively, of from about 1:1 to about 1:5 and recovering the resulting thioether product.

14. A process as in claim 13, wherein the molar ratio of (a) to (b) is about 1:3.

15. A process for obtaining 1-[4-α-(2,4-di-(t)-amylphenoxy)-butyramido phenyl]-3-pyrrolyl-4-(1-phenyl tetrazolyl seleno)-5-pyrazolone comprising contacting about 0.06 mole of the 4,4-dibromo precursor with about 0.02 mole of 1-phenyltetrazolyl-5-selenol in the presence of tetrahydrofuran reaction solvent at about 20°C., and recovering the resulting selenium ether product.

16. A process as in claim 15 wherein the molar ratio of (a) to (b) is about 1:3.

* * * * *